(12) United States Patent
Perkins et al.

(10) Patent No.: US 9,872,679 B2
(45) Date of Patent: Jan. 23, 2018

(54) LOCALLY REVERSIBLE BARBED SUTURES

(71) Applicant: Ethicon, Inc., Somerville, NJ (US)

(72) Inventors: Jason T. Perkins, Easton, PA (US); Mark T. Mooney, Johns Creek, GA (US); Jonathan B. Gabel, Randolph, NJ (US)

(73) Assignee: Ethicon, Inc., Somerville, NJ (US)

( * ) Notice: Subject to any disclaimer, the term of this patent is extended or adjusted under 35 U.S.C. 154(b) by 509 days.

(21) Appl. No.: 13/759,236

(22) Filed: Feb. 5, 2013

(65) Prior Publication Data

US 2014/0222071 A1  Aug. 7, 2014

(51) Int. Cl.
*A61B 17/06* (2006.01)
*A61B 17/04* (2006.01)

(52) U.S. Cl.
CPC .......... *A61B 17/06166* (2013.01); *A61B 2017/0417* (2013.01); *A61B 2017/0608* (2013.01); *A61B 2017/06176* (2013.01)

(58) Field of Classification Search
CPC ..... A61B 17/06; A61B 17/04; A61B 17/0401; A61B 2017/0412; A61B 17/06166; A61B 2017/0427; A61B 2017/06176; A61B 2017/0608; A61B 2017/0417
USPC ........................................................ 606/228
See application file for complete search history.

(56) References Cited

U.S. PATENT DOCUMENTS

| | | |
|---|---|---|
| 5,931,855 A | 8/1999 | Buncke |
| 7,468,068 B2 | 12/2008 | Kolster |
| 7,850,894 B2 | 12/2010 | Lindh, Sr. et al. |
| 8,210,085 B2 | 7/2012 | Lindh, Sr. et al. |
| 8,216,497 B2 | 7/2012 | Lindh, Sr. et al. |
| 8,226,684 B2 | 7/2012 | Nawrocki et al. |
| 2003/0149447 A1 | 8/2003 | Morency |
| 2007/0257395 A1 | 11/2007 | Lindh et al. |

(Continued)

FOREIGN PATENT DOCUMENTS

| | | |
|---|---|---|
| DE | 4302895 | 8/1994 |
| EP | 1857236 A1 | 11/2007 |

(Continued)

OTHER PUBLICATIONS

Tangent: definition of tangent in Oxford dictionary (American English) (US), date accessed Nov. 6, 2015, http://www.oxforddictionaries.com/us/definition/american_english/tangent.*

(Continued)

*Primary Examiner* — Christopher L Templeton
*Assistant Examiner* — George J Ulsh
(74) *Attorney, Agent, or Firm* — Doherty IP Law Group LLC

(57) ABSTRACT

A wound closure device includes a flexible filament having a first end, a second end, and a longitudinal axis extending between the first and second ends. A plurality of barbs project outwardly from the flexible filament. Each barb has a base connected with the flexible filament, a blunt tip spaced from the base, a leading edge extending between the base and the blunt tip and facing toward the first end of the flexible filament, and a trailing edge extending between the base and the tip and facing toward the second end of the flexible filament. The trailing edge of the barb and the longitudinal axis of the flexible filament define an angle of at least 68° that opens toward the second end of the flexible filament.

18 Claims, 12 Drawing Sheets

(56) References Cited

U.S. PATENT DOCUMENTS

| | | |
|---|---|---|
| 2008/0312688 A1 | 12/2008 | Nawrocki et al. |
| 2009/0312791 A1 | 12/2009 | Lindh et al. |
| 2010/0146770 A1 | 6/2010 | Morency et al. |
| 2011/0093010 A1 | 4/2011 | Genova et al. |
| 2011/0106152 A1 | 5/2011 | Kozlowski |
| 2012/0101526 A1* | 4/2012 | Bennett .............. A61B 17/0401 606/232 |
| 2013/0085525 A1 | 4/2013 | Nawrocki et al. |

FOREIGN PATENT DOCUMENTS

| | | |
|---|---|---|
| EP | 1858243 A1 | 11/2007 |
| EP | 1867288 A1 | 12/2007 |
| GB | 1091282 | 11/1967 |
| WO | 9107916 | 6/1991 |

OTHER PUBLICATIONS

International Search Report for International Application No. PCT/US2014/013380, dated Aug. 13, 2014, 8 pages.

* cited by examiner

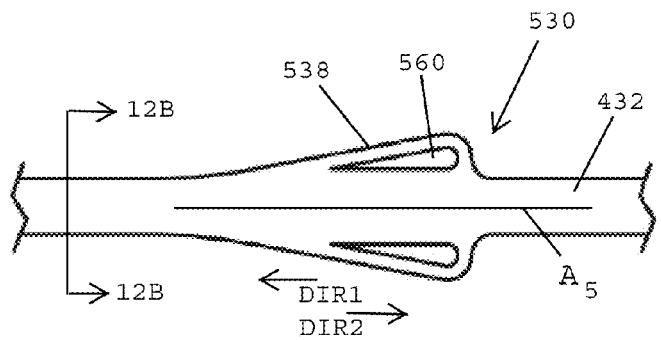
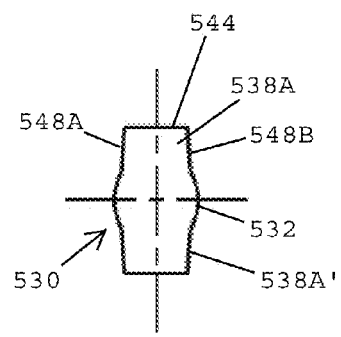
FIG. 12A
FIG. 12B
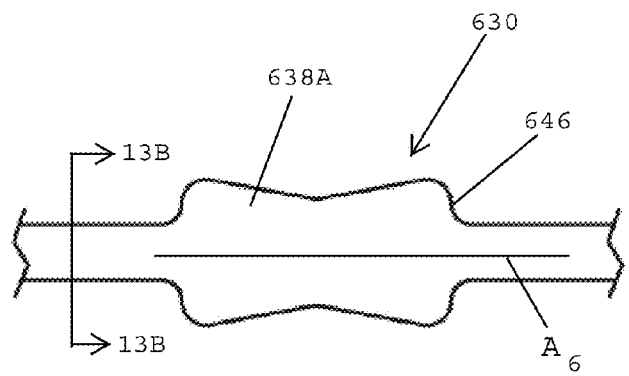
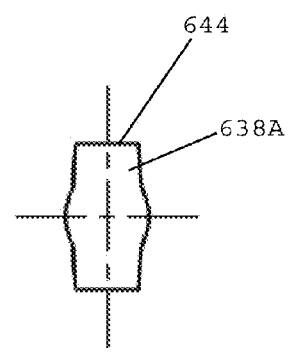
FIG. 13A
FIG. 13B
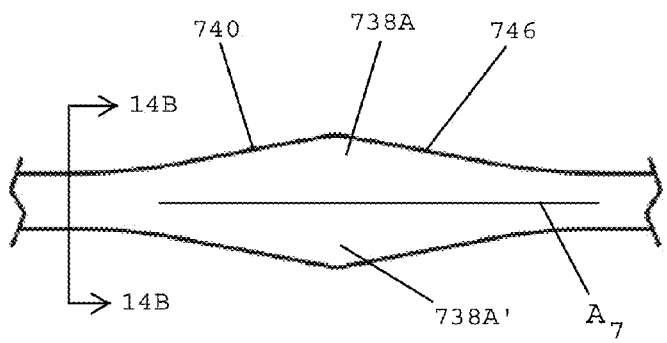
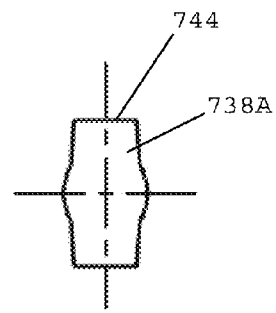
FIG. 14A
FIG. 14B

LOCALLY REVERSIBLE BARBED SUTURES

BACKGROUND OF THE INVENTION

Field of the Invention

The present invention generally relates to the field of surgical sutures, and more specifically relates to surgical sutures having barbs.

Description of the Related Art

Surgical sutures are used to close wounds and surgical incisions, and to repair damaged or severed muscles, vessels, and tissue. Typically, the suture is attached at one end to a needle, and the needle is drawn through tissue to form one or more loops holding the tissue together. The suture is subsequently tied off using one or more knots so that the tissue will remain drawn together.

The approximation of subcutaneous and dermal tissue layers are directly related to the final cosmetic outcome of an incision. Ideally, the tissue edges are aligned and apposed under minimal tension, which directly contributes to the degree of scar formation and the appearance of the closure.

Although conventional surgical sutures are very effective and reliable for closing wounds, additional sutures have been developed for use during certain types of medical procedures. One new type of suture, barbed sutures, have projecting barbs that allow the suture to be used to close wounds, approximate tissue, tighten tissue, and attach prosthetic devices—all without using knots. Barbed sutures achieve proper tensioning and fixation by applying tension to the suture. For example, U.S. Pat. No. 5,931,855 discloses barbed sutures that are used for cosmetic procedures such as brow-lifts and face-lifts.

Barbed sutures lend themselves to closure of subcutaneous and dermal tissue layers by providing speed and ease of use, no knot-related complications, even distribution of tension along or across the incision, and adequate wound holding strength to keep the tissue edges aligned throughout the critical wound healing period.

Existing barbed sutures allow for the passage of a barbed suture through tissue in a first direction to minimize drag, while maximizing holding strength in an opposite, second direction. These existing barbed sutures are not designed to be locally reversible without causing tissue trauma and plastic deformation and damage to the barbs themselves rendering them unable to adequately approximate tissue. Additionally, existing barbed suture designs are prone to damage because the barbs are cut into a monofilament suture, which essentially forms a hinge holding the barb to the monofilament. If a barbed suture "bite" is misplaced intra-operatively, a surgeon's only recourse is to cut the misplaced suture and continue the stitch pattern with a new barbed suture.

In spite of the above advances, there remains a need for barbed sutures that are locally reversible, that allow for passage of the barbed suture through tissue in two directions without causing trauma to the tissue or damaging the barbs, and that provide adequate tissue holding strength suitable to approximate tissue.

SUMMARY OF THE INVENTION

In one embodiment, a "locally reversible" barbed suture includes a flexible filament having a plurality of barbs projecting from the flexible filament whereby the barbs have a leading edge, a trailing edge, and a blunt tip, and whereby the trailing edge defines an angle of at least 68° relative to the longitudinal axis of the filament.

In one embodiment, a "locally reversible" barbed suture includes a flexible filament having a plurality of barbs projecting from the flexible filament, whereby the barbs have a leading edge, a trailing edge, and a tip each having a radius whereby the radius of the barb tip forms a blunt surface, and a line perpendicular to the flexible filament passes tangentially to the outer curvature formed by each radius.

In one embodiment, a barbed suture is capable of being passed through tissue in one direction with minimal resistance (defined by tissue drag force) and passed through tissue in an opposite direction with greater resistance (defined by barb holding force) without causing trauma to the tissue.

In one embodiment, a locally reversible wound closure device preferably includes a flexible filament having a first end, a second end, and a longitudinal axis extending between the first and second ends. The wound closure device includes a plurality of barbs projecting outwardly from the flexible filament, each barb desirably having a base connected with the flexible filament, a blunt tip spaced from the base, a leading edge extending between the base and the blunt tip and facing toward the first end of the flexible filament, and a trailing edge extending between the base and the tip and facing toward the second end of the flexible filament. In one embodiment, the trailing edge of the barb and the longitudinal axis of the flexible filament define an angle of at least 68° that opens toward the second end of the flexible filament. In one embodiment, the trailing edge of the barb and the longitudinal axis of the flexible filament desirably define an angle of at least 90° that opens toward the second end of the flexible filament.

In one embodiment, the leading edge of the barb and the longitudinal axis of the flexible filament preferably define a first obtuse angle facing the first end of the flexible filament, and the trailing edge of the barb and the longitudinal axis of the flexible filament preferably define a second obtuse angle facing the second end of the flexible filament.

In one embodiment, the leading edge of the barb defines a concave surface having a radius of about 0.090 inches, and the blunt tip defines a convex surface having a radius of about 0.004 inches. In one embodiment, the barb preferably has a transition surface extending between the trailing edge of the barb and the flexible filament. In one embodiment, the transition surface desirably defines a concave surface having a radius of about 0.003 inches.

In one embodiment, the flexible filament has a length and the barbs are evenly spaced along the length of the flexible filament. In one embodiment, the blunt tips of the evenly spaced barbs desirably define a tip-to-tip pitch of about 0.070-0.080 inches. In other embodiments, however, the tip-to-tip pitch may be greater and still fall within the scope of the present invention.

In one embodiment, the plurality of barbs includes pairs of barbs that are evenly spaced along the length of the flexible filament. In one embodiment, the barbs in each pair are aligned with one another. In one embodiment, a pair of aligned barbs extending outwardly from a flexible filament may lie in the same plane. In one embodiment, a pair of aligned barbs extending outwardly from a flexible filament may lie in different planes. The aligned barbs in each pair preferably project away from one another and are disposed on opposite sides of the flexible filament. In one embodiment, the distance between the tips of an aligned pair of barbs is about 19-30 mils or about 0.0190.030 inches. In one embodiment, the distance between the tips of an aligned pair of barbs is about 21 mils or about 0.021 inches.

In one embodiment, the barbs extending outwardly from opposite sides of the flexible filament are not aligned with one another and are staggered relative to one another along the length of the flexible filament. In one embodiment, the staggered barbs may lie in a single plane. In one embodiment, the staggered barbs may lie is different planes.

In one embodiment, the bases of the barbs are thicker than the tips of the barbs, and each barb has side walls that taper inwardly between the base and the tip. In one embodiment, each of the side walls tapers inwardly at an angle of about 3-5°.

In one embodiment, a stop element is connected with the second end of the flexible filament. The stop element preferably has a leading edge that extends substantially perpendicular to the longitudinal axis of the flexible filament. In one embodiment, a needle may be connected with the first end of the flexible filament.

In one embodiment, a wound closure device desirably includes a flexible filament having a first end, a second end, and a longitudinal axis extending between the first and second ends, and a plurality of barbs projecting from the flexible filament. In one embodiment, each barb desirably has a base connected with the flexible filament, a tip spaced from the base, the tip having a blunt surface with a radius, a leading edge extending between the base and the tip and facing toward the first end of the flexible filament, and a trailing edge extending between the base and the tip and facing toward the second end of the flexible filament. In one embodiment, each barb desirably includes a transition surface extending between the trailing edge of the barb and the flexible filament, whereby a line perpendicular to the longitudinal axis of the flexible filament passes tangentially through both the transition surface of the barb and the radius of the blunt surface of the tip.

In one embodiment, a wound closure device preferably includes a flexible filament having a first end, a second end, and a longitudinal axis extending between the first and second ends. A plurality of barbs preferably project outwardly from the flexible filament, each barb desirably having a base connected with the flexible filament, a blunt tip spaced from the base, a leading edge extending between the base and the blunt tip and facing toward the first end of the flexible filament, a trailing edge extending between the blunt tip and the base and facing toward the second end of the flexible filament, and a transition surface extending between the trailing edge and the flexible filament. In one embodiment, the leading edge preferably defines a concave surface having a radius of about 0.090 inches, the blunt tip preferably defines a convex surface having a radius of about 0.004 inches, and the transition surface preferably has a radius of about 0.004 inches. The trailing edge of the barb and the longitudinal axis of the flexible filament desirably define an angle of at least 68° that opens toward the second end of the flexible filament. In one embodiment, the trailing edge angle is 90° or greater to define an obtuse angle that opens toward the second end of the flexible filament.

In one embodiment, the barbs are evenly spaced along the length of the flexible filament and define a longitudinal tip-to-tip pitch of about 0.070-0.080 inches. In one embodiment, the plurality of barbs desirably includes pairs of barbs that are aligned with one another and evenly spaced along the length of the flexible filament. The barbs in each pair desirably project away from one another and are disposed on opposite sides of the flexible filament. The distance between the tips of aligned barbs on opposite sides of the flexible filament may be about 19-30 mils or about 0.019-0.030 inches, and more preferably about 21 mils or about 0.021 inches.

In one embodiment, the slopes of the leading and trailing portions of the barbs are gradual, which allows for local adjustments in tissue.

In one embodiment, a shallow undercut allows barbs to act more like buttresses rather than hinges (as is the case with existing barb designs).

In one embodiment, the barbs are not intended to flex, but rather serve as points of resistance along the length of the suture, which allows for local reversibility and/or adjustments to the placement of the suture The design of the barbs is such that it is easily manufacturable via known punching processes, as described in commonly assigned U.S. Patent Application Publication No. 2009/0312791, the disclosure of which is hereby incorporated by reference herein.

These and other preferred embodiments of the present invention will be described in more detail below.

BRIEF DESCRIPTION OF THE DRAWING

FIG. 12A shows a side-elevation view of a barbed suture having collapsible barbs, in accordance with another embodiment of the present invention.

FIG. 12B shows a cross-sectional view of the barbed suture of FIG. 12A taken along line 12B-12B thereof.

FIG. 13A shows a side-elevation of a barbed suture, in accordance with one embodiment of the present invention.

FIG. 13B shows a cross-sectional view of the barbed suture of FIG. 13A taken along line 13B-13B thereof.

FIG. 14A shows a barbed suture, in accordance with yet another embodiment of the present invention.

FIG. 14B shows a cross-sectional view of the barbed suture of FIG. 14A taken along line 14B-14B thereof.

DETAILED DESCRIPTION

Figure 1A:
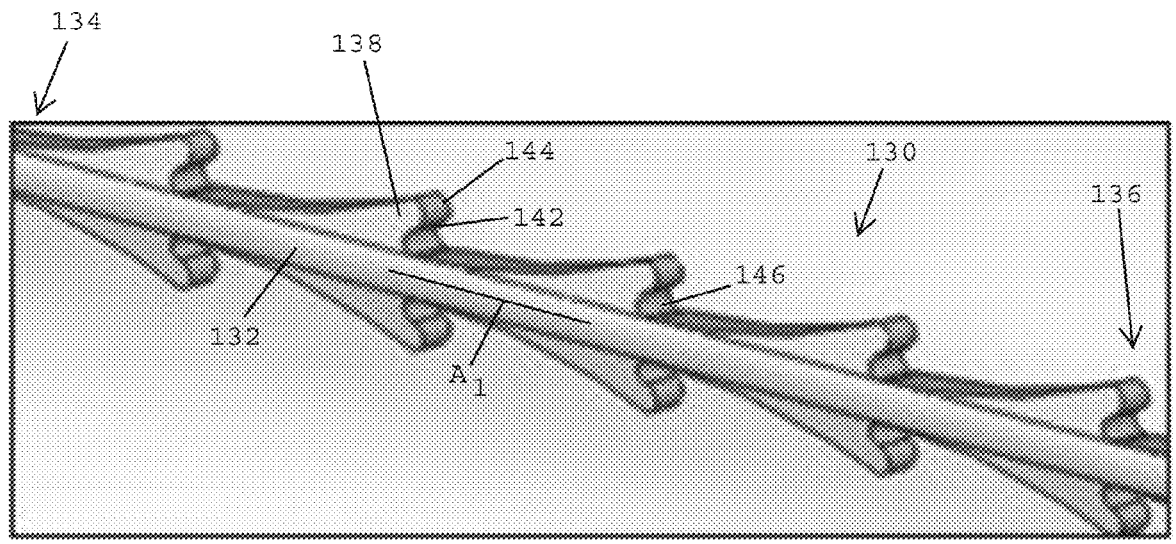
FIG. 1A shows a perspective view of a first barbed suture.
Figure 1B:
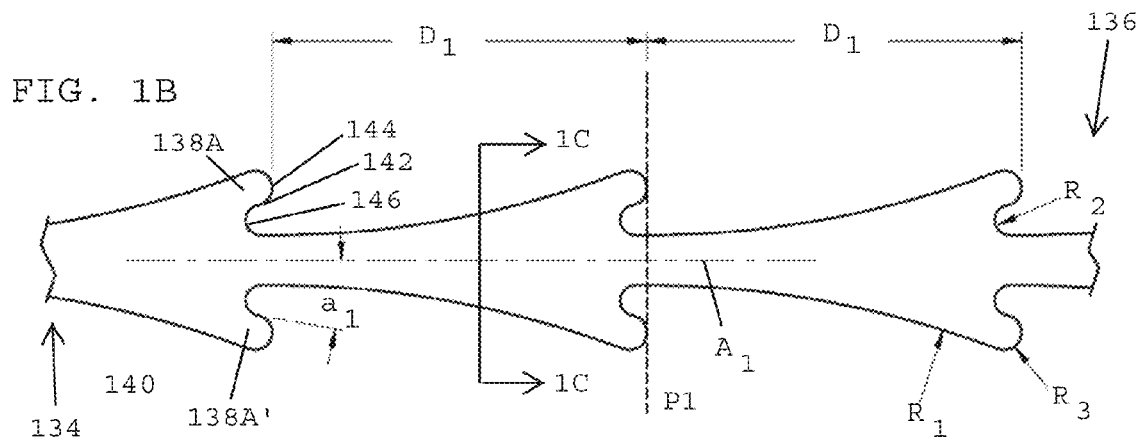
FIG. 1B shows a side-elevation view of the first barbed suture shown in FIG. 1A.
Figure 1C:
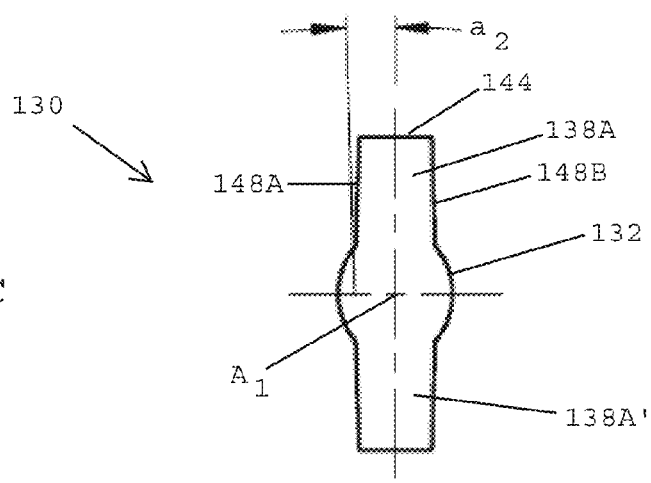
FIG. 1C shows a cross-sectional view of the first barbed suture of FIG. 1B taken along line 1C-1C thereof.

Referring to FIGS. 1A-1C, a first barbed suture 130, designated SB1, includes a flexible filament 132 having a first end 134 (i.e., leading end), a second end 136 (i.e., trailing end), and a longitudinal axis $A_1$ that extends from the first end 134 to the second end 136. The barbed suture 130 includes a plurality of barbs 138 that project outwardly from the flexible filament 132 (i.e., away from the longitudinal axis $A_1$) and extend toward the second end 136 of the flexible filament 132. Each barb 138 has a leading edge 140 that faces toward the first end 134 of the filament, a trailing edge 142 that faces toward the second end 136 of the filament, and a barb tip 144 that is located between the leading and trailing edges of the barb. Each barb 138 also has a transition surface 146 that is located between the trailing edge 142 of the barb 138 and the outer surface of the flexible filament 132 for providing a transition zone between the trailing edge 142 of the barb 138 and the flexible filament.

The plurality of barbs 138 are paired so that a first barb 138A extends from a first side of the filament 132 and a second barb 138A', is aligned with the first barb 138A, extends from an opposite, second side of the filament 132. Multiple pairs of barbs 138A, 138A', 138B, 138B', 138C, 138C', etc. are evenly spaced along the length or longitudinal axis $A_1$ of the flexible filament 132 so that adjacent barbs 138 on the same side of the filament have a tip-to-tip distance $D_1$ of about 0.070-0.080 inches. The trailing edge 142 of the barb 138 extends away from the longitudinal axis $A_1$ of the filament 132 at an angle $\alpha_1$, designated the trailing edge angle, of about 10°. The leading edge 140 of the barb 138 includes a concave surface defining a radius $R_1$ of about 0.200 inches. The transition surface 146 between the trailing edge 142 of the barb 138 and the filament 132 defines a concave surface forming an undercut having a radius $R_2$ of about 0.003 inches. The barb tip 144 has a blunt convexly curved surface having a radius $R_3$ of about 0.004 inches.

The distal-most surface of the blunt tip 144 is closer to the second end 136 of the filament 132 than is the transition surface 146. As a result, a line $P_1$ (FIG. 1B) that is perpendicular to the longitudinal axis $A_1$ of the flexible filament 132 and that passes tangentially through the convexly curved surface of the blunt tip 144 is spaced distally from the transition surface 146. Stated another way, the perpendicular line $P_1$ does not pass through both the distal-most surface of the blunt tip 144 and the transition surface 146. Stated yet another way, the undercut of the transition surface 146 is closer to the first end 134 of the filament 132 and the distal-most surface of the blunt tip 144 is closer to the second end 136 of the filament 132.

FIG. 1C shows the flexible filament 132 of the first barbed suture 130 extending along the longitudinal axis $A_1$. The paired barbs 138A, 138A' extend away from one another on opposite sides of the flexible filament 132. The first barb 138A has first and second lateral side walls 148A, 148B that taper inwardly toward one another between the core of the flexible filament 132 and the blunt tip 144 of the first barb 138A. The inwardly tapering first lateral side wall 148A defines an angle $\alpha_2$ of about 2°. The inwardly tapering second lateral side wall 148A also defines an angle of about 2°. Each lateral side wall of the second barb 138A' also tapers inwardly at an angle of about 2°.

Figure 2A:
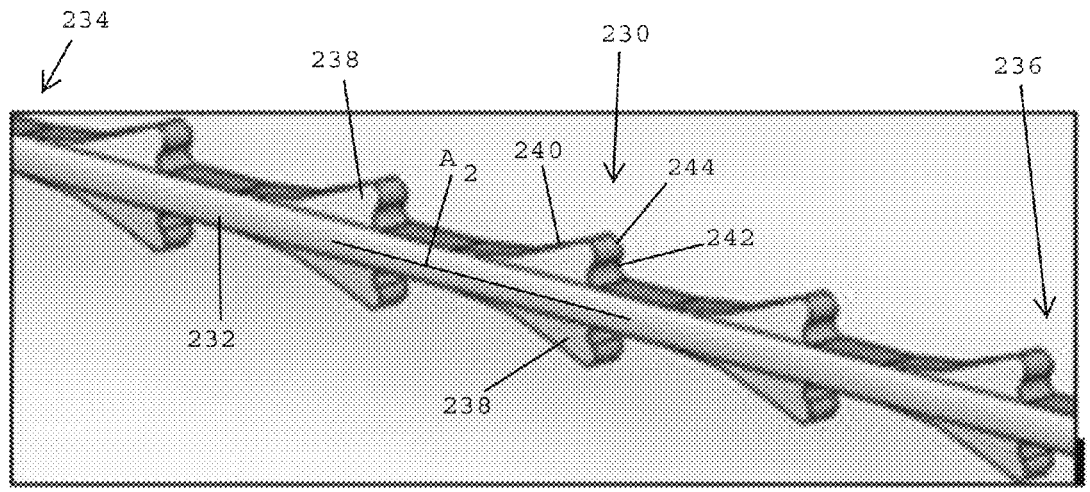
FIG. 2A shows a perspective view of a second barbed suture.
Figure 2B:
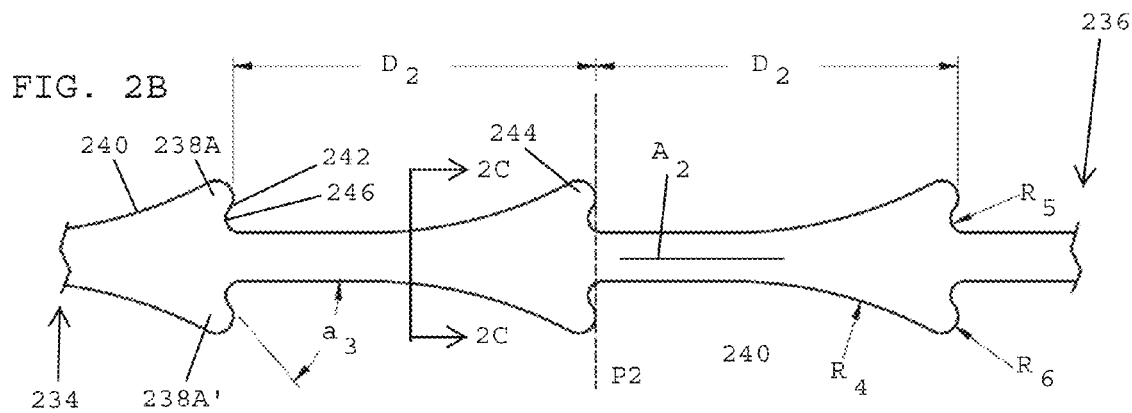
FIG. 2B shows a side-elevation view of the second barbed suture shown in FIG. 2A.
Figure 2C:
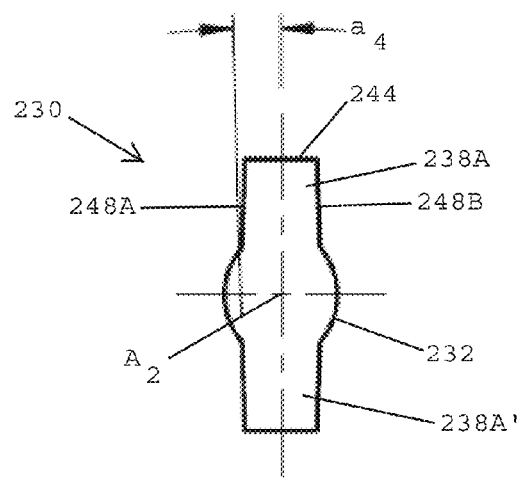
FIG. 2C shows a cross-sectional view of the second barbed suture of FIG. 2B taken along line 2C-2C thereof.

Referring to FIGS. 2A-2C, a second barbed suture 230, designated SB2, includes a flexible filament 232 with a first end 234, a second end 236, and a longitudinal axis $A_2$ that extends from the first end 234 to the second end 236. The barbed suture 230 includes a plurality of barbs 238 that project outwardly from the flexible filament 232 (i.e., away from the longitudinal axis $A_2$) and extend toward the second end 236 of the flexible filament 232. Each barb 238 has a leading edge 240 that faces toward the first end of the filament, a trailing edge 242 that faces toward the second end of the filament, and a barb tip 244 that is located between the leading and trailing edges of the barb. Each barb 238 also has a transition surface 246 that is located between the trailing edge 242 of the barb 238 and the outer surface of the flexible filament 232 for providing a transition zone between the trailing edge of the barb and the flexible filament.

The plurality of barbs 238 are paired so that a first barb 238A extends from a first side of the filament 232 and a second barb 238A', which is aligned with the first barb 238A, extends from an opposite, second side of the filament 232. Each of the paired barbs 138A, 138A', 138B, 138B', 138C, 138C', etc. are evenly spaced along the length or longitudinal axis $A_2$ of the flexible filament 232 so that adjacent barbs on the same side of the filament have a tip-to-tip distance $D_2$ of about 0.070-0.080 inches. The trailing edge 242 of the barb 238 extends away from the longitudinal axis $A_2$ of the filament 232 at an angle $\alpha_3$, designated a trailing edge angle, of about 49°. The leading edge 240 of the barb 238 includes a concave surface defining a radius $R_4$ of about 0.090 inches. The transition surface 246 between the trailing edge 242 of the barb 238 and the filament 232 defines a concave surface forming an undercut having a radius $R_5$ of about 0.003 inches. The barb tip 244 has a blunt, convexly curved surface having a radius $R_6$ of about 0.004 inches.

The distal-most surface of the blunt tip 244 is closer to the second end 236 of the filament 232 than is the transition surface 246. As a result, a line $P_2$ that is perpendicular to the longitudinal axis $A_2$ of the flexible filament 232 and that passes tangentially through the convexly curved surface of the blunt tip 244 is spaced distally from the transition surface 246 (i.e., is closer to the second end 236 of the filament 132).

Stated another way, the perpendicular line $P_2$ does not pass through both the distal-most surface of the blunt tip 244 and the transition surface 246.

FIG. 2C shows the flexible filament 232 of the second barbed suture 230 extending along the longitudinal axis $A_2$. The paired barbs 238A, 238A' extend away from one another on opposite sides of the flexible filament 232. The first barb 238A has first and second lateral side walls 248A, 248B that taper inwardly toward one another between the core of the flexible filament 232 and the blunt tip 244 of the first barb. The inwardly tapering first lateral side wall 248A defines an angle $\alpha_4$ of about 2°. The inwardly tapering second lateral wall 248B also defines an angle of about 2°. Each of the lateral side walls of the second barb 238A' also taper inwardly at an angle of about 2°.

Referring to FIGS. 3A-3D, in one embodiment of the present invention, a third barbed suture 330, designated SB3, includes a flexible filament 332 with having a first end 334, a second end 336, and a longitudinal axis $A_3$ that extends from the first end 334 to the second end 336. The barbed suture 330 includes a plurality of barbs 338 that project outwardly from the flexible filament 332 (i.e., away from the longitudinal axis $A_3$) and extend toward the second end 336 of the flexible filament 332. In one embodiment, the plurality of projections may extend outwardly from the flexible filament by approximately 6-25 mils or 0.006-0.025 inches. Each barb 338 has a leading edge 340 that faces toward the first end 334 of the filament, a trailing edge 342 that faces toward the second end of the filament, and a barb tip 344 that is located between the leading and trailing edges of the barb. Each barb 338 also has a transition surface 346 that is located between the trailing edge 342 of the barb 338 and the outer surface of the flexible filament 332 for providing a transition zone between the trailing edge of the barb and the flexible filament.

The plurality of barbs 338 are paired so that a first barb 338A extends from a first side of the filament 332 and a second barb 338B, which is aligned with the first barb 338A, extends from an opposite, second side of the filament 332. Each of the paired barbs 138A, 138A', 138B, 138B', 138C, 138C', etc. are evenly spaced along the length or longitudinal axis $A_3$ of the flexible filament 332 so that adjacent barbs on the same side of the filament have a tip-to-tip distance $D_3$ of about 0.070-0.080 inches, and more preferably about 0.075 inches. The trailing edge 342 of the barb 338 extends away from the longitudinal axis $A_3$ of the filament 332 at an angle $\alpha_5$, designated the trailing edge angle, of about 68°. The leading edge 340 of the barb 338 includes a concave surface defining a radius $R_7$ of about 0.090 inches. The transition surface 346 between the trailing edge 342 of the barb 338 and the filament 332 defines a concave surface having a radius $R_8$ of about 0.003 inches. The barb tip 344 has a blunt convexly curved surface having a radius $R_9$ of about 0.004 inches.

In one embodiment, the distal-most surface of the blunt tip 344 and the transition surface 346 are in substantial alignment with one another. As a result, a line $P_3$ that is perpendicular to the longitudinal axis $A_3$ of the flexible filament 332 and that passes tangentially through the convexly curved surface of the blunt tip 344 also passes tangentially through the transition surface 346. Stated another way, the perpendicular line $P_3$ passes tangentially through both the distal-most surface of the blunt tip 344 and the transition surface 346, and the transition surface 346 does not have the "undercut" found in the transition surface region of the barbs of the first and second barbed sutures 130 (SB1) and 230 (SB2).

Figure 3A:
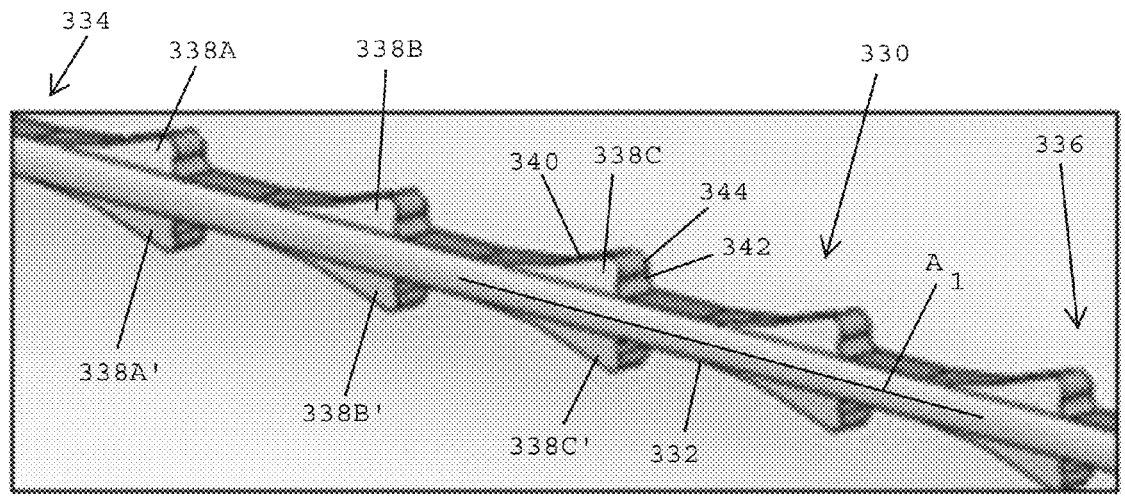
FIG. 3A shows a perspective view of a third barbed suture, in accordance with one embodiment of the present invention.
Figure 3B:
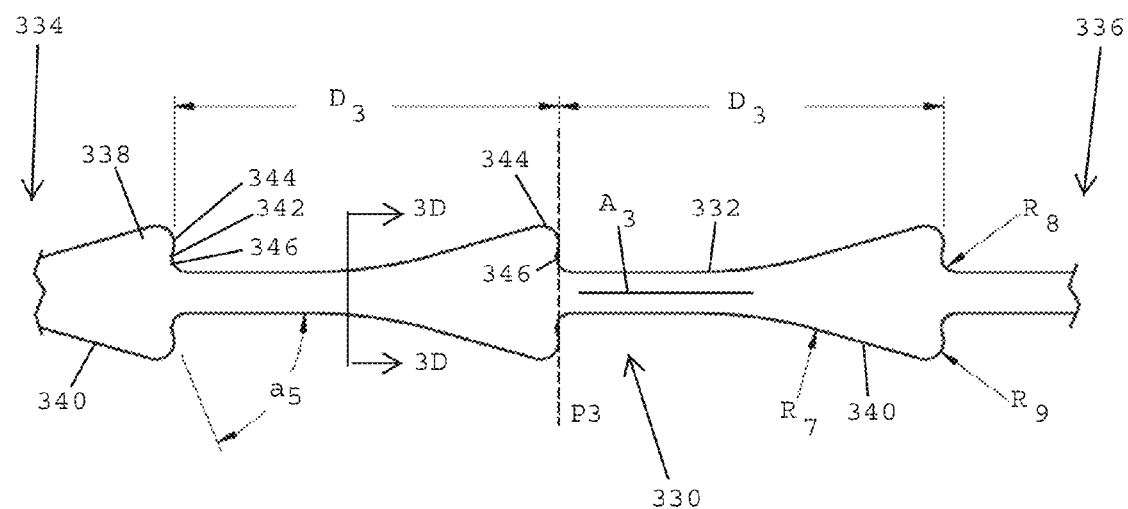
FIG. 3B shows a front-elevation view of the third barbed suture shown in FIG. 3A.
Figure 3C:
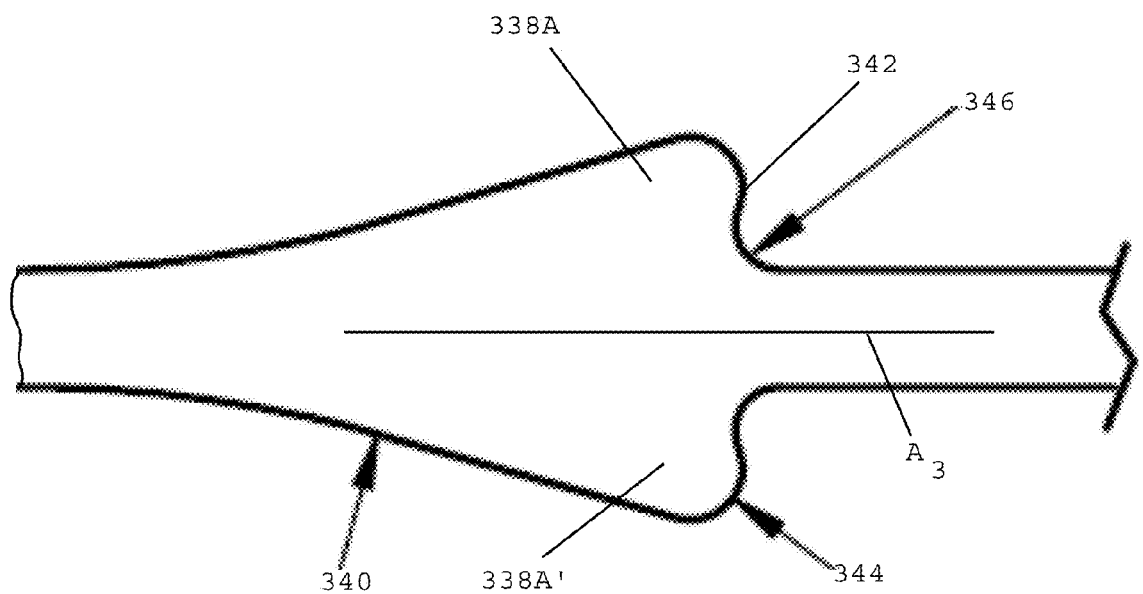
FIG. 3C shows a magnified view of a section of the third barbed suture shown in FIG. 3B.
Figure 3D:
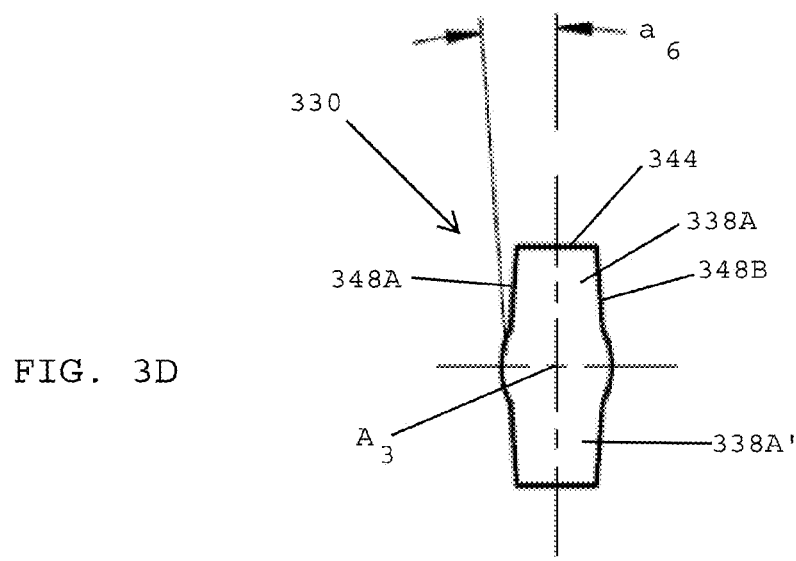
FIG. 3D shows a cross-sectional view of the third barbed suture of FIG. 3B taken along line 3D-3D thereof.

FIG. 3D shows the flexible filament 332 of the third barbed suture 320 extending along the longitudinal axis $A_3$. The paired barbs 338A, 338A' extend away from one another on opposite sides of the flexible filament 332. The first barb 338A has first and second lateral side walls 348A, 348B that taper inwardly toward one another between the core of the flexible filament 332 and the blunt tip 344 of the first barb. The inwardly tapering first lateral side wall 348A defines an angle $\alpha_6$ of about 4°. The inwardly tapering second lateral side wall 348A also defines an angle of about 4°. Each of the lateral side walls of the second barb 338A' also taper inwardly at an angle of about 4°.

Referring to FIGS. 4A-4D, in one embodiment of the present invention, a fourth barbed suture 430, designated SB4, preferably includes a flexible filament 432 having a first end 434, a second end 436, and a longitudinal axis $A_4$ that extends from the first end 434 to the second end 436 of the filament. The barbed suture 430 includes a plurality of barbs 438 that project outwardly from the flexible filament 432 (i.e., away from the longitudinal axis $A_4$) and extend toward the second end 436 of the flexible filament 432. Each barb 438 has a leading edge 440 that faces toward the first end 434 of the filament, a trailing edge 442 that faces toward the second end of the filament, and a barb tip 444 that is located between the leading and trailing edges of the barb. Each barb 438 also has a transition surface 446 that is located between the trailing edge 442 of the barb 438 and the outer surface of the flexible filament 432 for providing a transition zone between the trailing edge of the barb and the flexible filament.

In one embodiment, the plurality of barbs 438 are paired so that a first barb 438A extends from a first side of the filament 432 and a second barb 438A', which is aligned with the first barb 438A, extends from an opposite, second side of the filament 432. In one embodiment, each of the paired barbs i.e., 438A, 438A', 438B, 438B', 438C, 438C' 438D, 438D', etc., are evenly spaced along the length or longitudinal axis $A_4$ of the flexible filament 432 so that adjacent barbs on the same side of the filament have a tip-to-tip distance $D_4$ of about 0.070-0.080 inches, and more preferably about 0.075 inches. The trailing edge 442 of the barb 438 extends away from the longitudinal axis $A_4$ of the filament 432 at an angle $\alpha_7$, designated the trailing edge angle, of about 90°. The leading edge 440 of the barb 438 includes a concave surface defining a radius $R_{10}$ of about 0.090 inches. The transition surface 446 between the trailing edge 442 of the barb 438 and the filament 432 defines a concave surface having a radius $R_{11}$ of about 0.003 inches. The barb tip 444 has a blunt, convexly curved surface having a radius $R_{12}$ of about 0.004 inches.

In one embodiment, the distal-most surface of the blunt tip 444 and the transition surface 446 are in substantial alignment with one another. As a result, a line $P_4$ that is perpendicular to the longitudinal axis $A_4$ of the flexible filament 432 and that passes tangentially through the convexly curved surface of the blunt tip 444 also passes tangentially through the transition surface 446. Stated another way, the perpendicular line $P_4$ passes through both the distal-most surface of the blunt tip 444 and the transition surface 446, and the transition surface 446 does not have the "undercut" found in the transition surface zone of the barbs of the first and second barbed sutures SB1 and SB2.

Figure 4A:
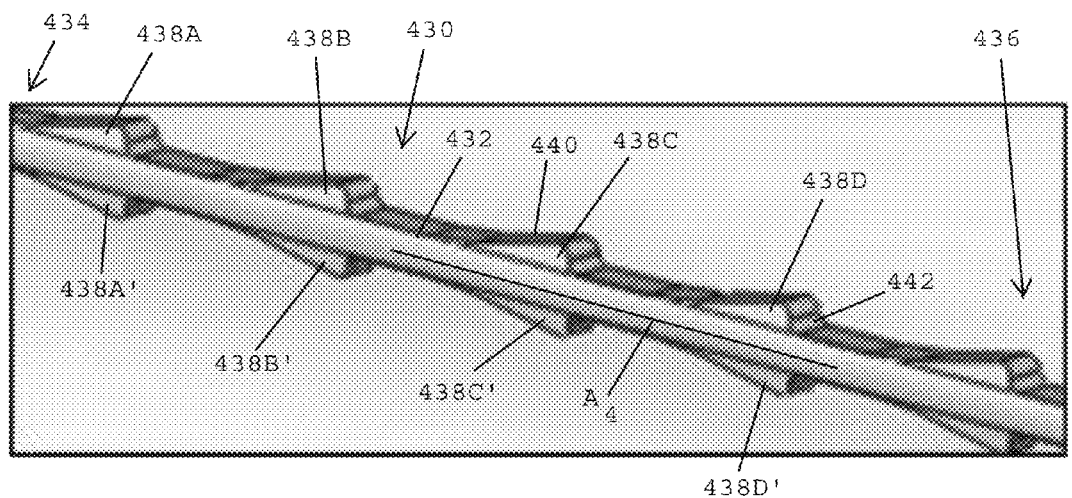
FIG. 4A shows a perspective view of a fourth barbed suture, in accordance with one embodiment of the present invention.
Figure 4B:
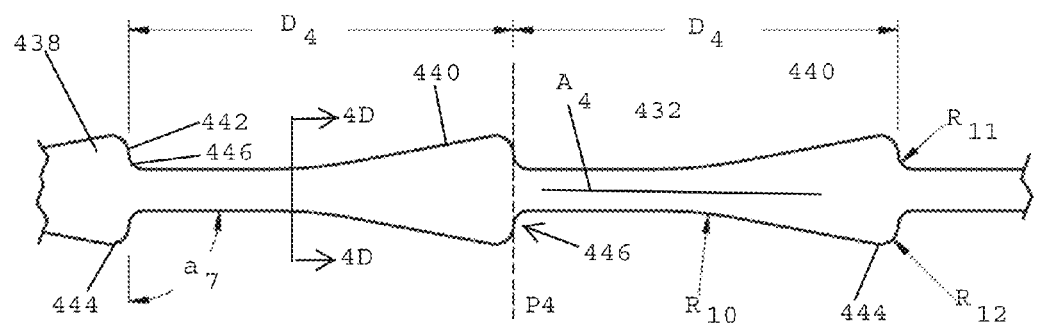
FIG. 4B shows a side-elevation view of the fourth barbed suture of FIG. 4A.
Figure 4C:
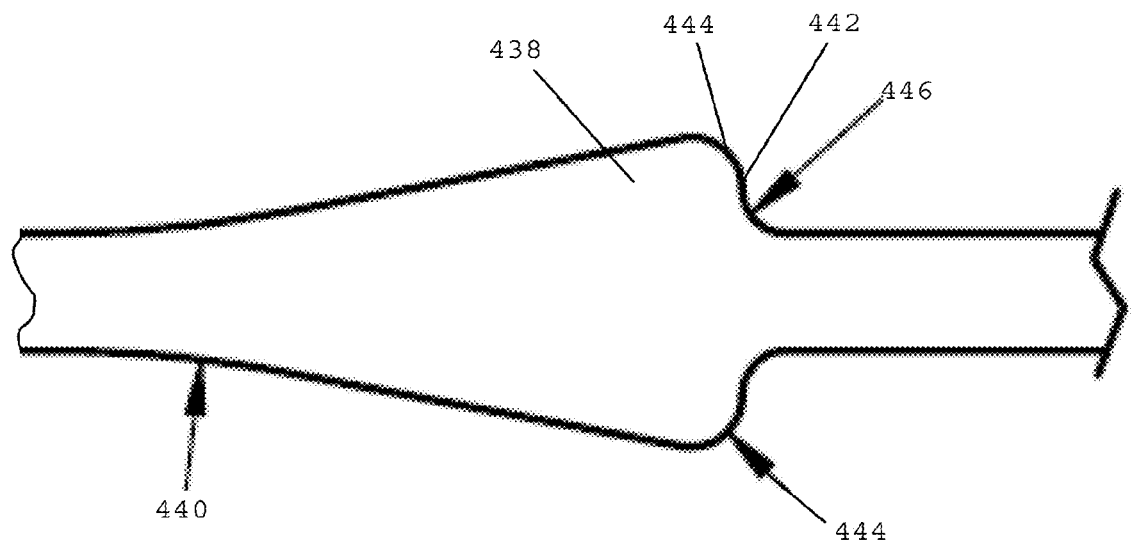
FIG. 4C shows a magnified view of a section of the fourth barbed suture shown in FIG. 4B.
Figure 4D:
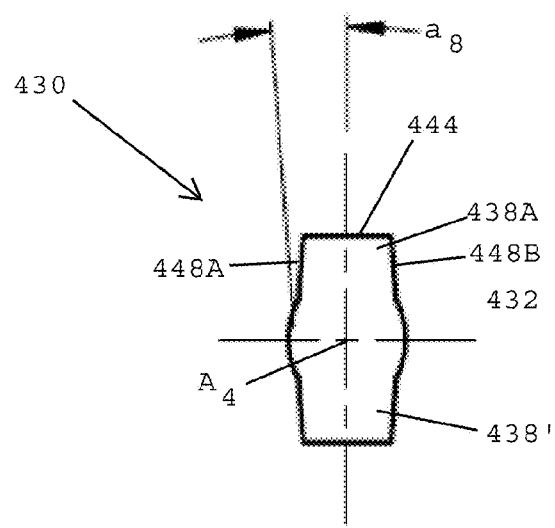
FIG. 4D shows a cross-sectional view of the fourth barbed suture of FIG. 4B taken along line 4D-4D thereof.

FIG. 4D shows the flexible filament 432 of the fourth barbed suture 430 extending along the longitudinal axis $A_4$. The paired barbs 438A, 438A' extend away from one another on opposite sides of the flexible filament 432. The first barb 438A has first and second lateral side walls 448A, 448B that taper inwardly toward one another between the core of the flexible filament 432 and the blunt tip 444 of the first barb. The inwardly tapering first lateral side wall 448A defines an angle $\alpha_8$ of about 4°. The inwardly tapering second lateral side wall 448B also defines an angle of about 4°. Each of the lateral side walls of the second barb 438A' also taper inwardly at an angle of about 4°.

In one embodiment, the barbed sutures may be formed by various techniques including press-forming, profile punching, laser cutting or the like as disclosed in commonly assigned U.S. Pat. Nos. 7,850,894, 8,216,497, and 8,226,684, and U.S. Patent Application Publication No. 2008/0312688, the disclosures of which are hereby incorporated by reference herein.

As disclosed in U.S. Pat. Nos. 7,850,894 and 8,201,497, a method for forming a barbed suture for surgical applications includes providing first and second female dies each having respective first and second top surfaces with first and second recesses formed therein. The first and second recesses are sized and shaped so that when aligned with one another, they together form a mold cavity having a predetermined shape. The predetermined shape includes a filament part extending along a length thereof, and a plurality of tissue holding barbs extending outwardly from the filament part. The method preferably includes providing a biocompatible, moldable material, such as polymeric material, placing the moldable material between the top surfaces of the first and second dies, and pressing the top surfaces of the first and second dies together until the top surfaces of the first and second dies are substantially in contact with one another and the recesses of the first and second dies substantially aligned to form the mold cavity, whereby the moldable material deforms and fills the cavity therebetween to form a barbed suture having the predetermined shape.

In one embodiment, the barbed sutures may be formed as disclosed in commonly assigned U.S. Pat. No. 8,226,684, the disclosure of which is hereby incorporated by reference herein. As disclosed in the '684 patent, a method of making barbed sutures includes providing a male die having a first clamping part and a second clamping part, and a female die having a first clamping part and a second clamping part. In one embodiment, during one stage of the process, the first and second clamping parts of the respective male and female dies are opened and an elongated shaft of biocompatible, moldable material is positioned between the first and second clamping parts. With the elongated shaft of moldable material positioned between the open clamping parts of the male die and the female die, the opposing clamping parts are closed to engage the outer surface of the elongated shaft of moldable material. In one embodiment, the male and female dies are heated to transfer heat to the elongated shaft of moldable material so that the elongated shaft is heated to a desired temperature for enabling the shaft to be molded by the male and female die.

In one embodiment, after the male and female die heat the elongated shaft of moldable material to a preferred molding temperature, the closed male die is moved relative to the closed female die to shape a portion of the elongated shaft into a protrusion or barb. In one embodiment, as the male die moves toward the female die, the overall length of the shaft is shortened. In one preferred embodiment, the die tooling moves relative to the shaft to compensate for the shortening of the shaft. In one embodiment, after the barb is formed, the barb is cooled while remaining in contact with the closed male and female dies. In one embodiment, the barb cools after being removed from engagement with the male and female dies. In one embodiment, the male and female dies are opened to expose the barb to ambient air, preferably for cooling. The above-described steps are repeated to form a plurality of barbs along the length of the elongated shaft.

In one embodiment, a filament winding assembly winds a plurality of filaments around a barbed suture, such as a barbed insert, to form a braided barbed suture, as disclosed in commonly assigned U.S. Pat. No. 8,210,085, the disclosure of which is hereby incorporated by reference herein.

In one embodiment, the barbs may be formed by cutting into the flexible filament or core using a mechanical cutting element, such as a blade, by cutting into the flexible filament or core using a laser, or by etching into the core using chemicals or energy.

In one embodiment, the barbed sutures disclosed herein may be made of conventional, biocompatible, absorbable materials, non-absorbable materials, and combinations of absorbable and non-absorbable materials. Preferred non-absorbable materials suitable for both the barbed sutures include polypropylene, a polymer blend of polyvinylidene fluoride and polyvinylidene fluoride-co-hexafluoropropylene, polyethylene, polyvinylidene fluoride (PVDF), polyesters, polyethylene terephthalate, glycol-modified polyethylene terephthalate, polytetrafluoroethylene, fluoropolymers, nylons etc. and the like, or copolymers of combinations thereof. Preferred absorbable polymeric materials suitable for the barbed sutures include polydioxanone, polyglactin, polyglycolic acid, copolymers of glycolide and lactide, polyoxaesters, and poliglecaprone. In certain preferred embodiments, these may include combinations of both absorbable and non-absorbable materials. In addition, metals or ceramics may be suitable for certain applications, such as instances where specific strength or corrosion resistance is necessary. In one preferred embodiment, the barbed sutures preferably includes a polymer blend of polyvinylidene fluoride and polyvinylidene fluoride-co-hexafluoropropylene material. In one embodiment, the barbed sutures may have surface modifications that include coatings, plasma treatments, therapeutics, and the like.

In one embodiment, the barbed sutures of the present invention are made using a non-absorbable polymeric material, and a non-absorbable multi-filament polyester suture, commonly sold under the trademark ETHIBOND EXCEL polyester suture by Ethicon, Inc. In one embodiment, a surgical needle may be attached to at least one end of a barbed suture. In one embodiment, surgical needles may be attached to both ends of the barbed suture. In one embodiment, a stopper may be secured to an end of the flexible filament. In one embodiment, a pledget, such as a Teflon® pledget, may be positioned in the middle of a barbed suture.

Figure 5:
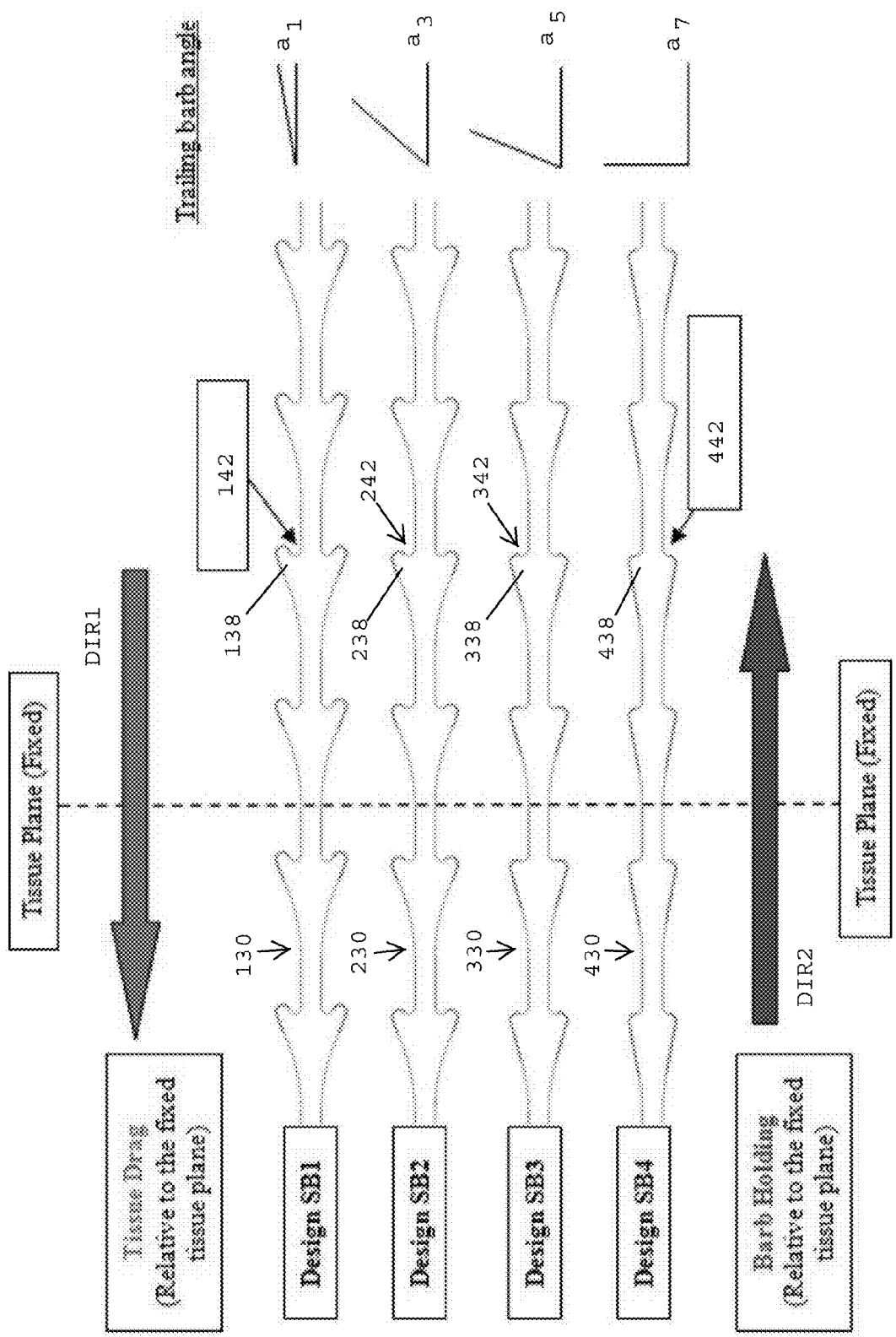
FIG. 5 shows a side-by-side comparison of the four barbed sutures shown in FIGS. 1A, 2A, 3A and 4A, respectively, passing through a tissue plane.

Referring to FIG. 5, the four different barbed sutures 130 (SB1), 230 (SB2), 330 (SB3), and 430 (SB4) described herein were passed through a fixed tissue plane to evaluate tissue drag and barb holding strength for each of the four barbed sutures. As noted above, the respective trailing edges 142, 242, 342, 442 of the barbs of the four barbed sutures 130, 230, 330, 430 have different trailing edge angles, which impacts both tissue drag and barb holding strength. The barbs 138 on the first barbed suture 130 have a trailing edge angle $\alpha_1$ of about 10°. The barbs 238 on the second barbed suture 230 have a trailing edge angle $\alpha_3$ of about 49°. The barbs 338 on the third barbed suture 330 have a trailing edge angle $\alpha_5$ of about 68°. The barbs 438 on the fourth barbed suture 430 have a trailing barb angle $\alpha_7$ of about 90°. Referring to FIG. 5, tissue drag relative to the fixed tissue plane is measured for each of the four barbed sutures 130, 230, 330, and 430 as the respective barbed sutures are advanced through the tissue in the direction designated DIR1. The barb holding strength relative to the fixed tissue plane is measured for each of the barbed sutures 130, 230, 330, and 430 as the respective barbed sutures are advanced through the tissue in the direction designated DIR2, which is opposite direction DIR1.

Example 1

Figure 6:
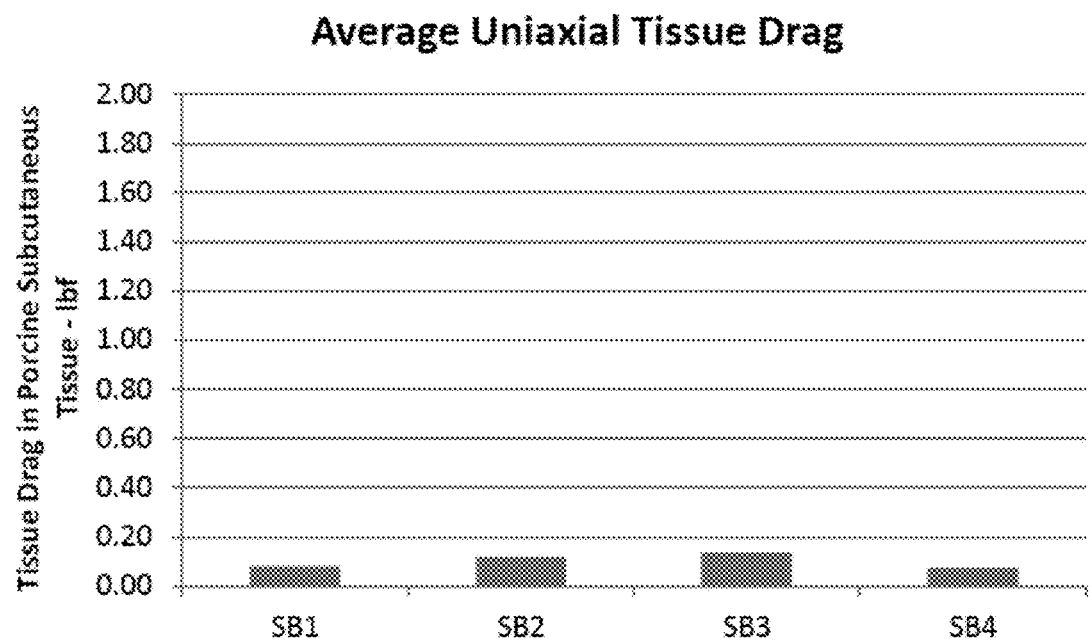
FIG. 6 shows a first graph plotting tissue drag for each of the four barbed sutures shown in FIG. 5.

Referring to FIGS. 5 and 6, in one embodiment, the four barbed sutures 130 (SB1), 230 (SB2), 330 (SB3), and 430 (SB4) were passed in the same direction (e.g., direction DIR1 in FIG. 5) through porcine subcutaneous tissue held in a fixture under a constant load applied by an Instron mechanical tester. More specifically, a drag force test was conducted to evaluate the drag force of the four barbed sutures as they are passed through tissue. During testing, the four barbed sutures 130 (SB1), 230 (SB2), 330 (SB3), and 430 (SB4) were not pulled through the tissue by the Instron mechanical tester at the same time. Each of the four barbed sutures 130 (SB1), 230 (SB2), 330 (SB3), and 430 (SB4) is tested individually so that only one of the four barbed sutures is pulled through the tissue by the Instron mechanical tester during any single test. During the test, the first end of each filament was introduced through a custom slotted fixture having a plane of tissue clamped in it. After the first end of each filament is passed through the tissue, the needle was removed, and the first end of each filament was secured in the upper grip of an Instron mechanical tester (5500 series or equivalent with 20 lb load cell). The needle attached to the barbed sutures was of the same type and dimension for each of the four barbed sutures designs. The Instron mechanical tester pulled each of the four barbed sutures through the tissue at 1 inch/min and the maximum drag force was recorded. The maximum load required to pass each of the four barbed sutures through the tissue is plotted in the graph shown in FIG. 6. The tissue drag for the first barbed suture 130 (SB1) was about 0.075 lbf. The tissue drag for the second barbed suture 230 (SB2) was about 0.125 lbf. The tissue drag for the third barbed suture 330 (SB3) was about 0.150 lbf. The tissue drag for the fourth barbed suture 430 (SB4) was about 0.075 lbf.

Example 2

Figure 7:
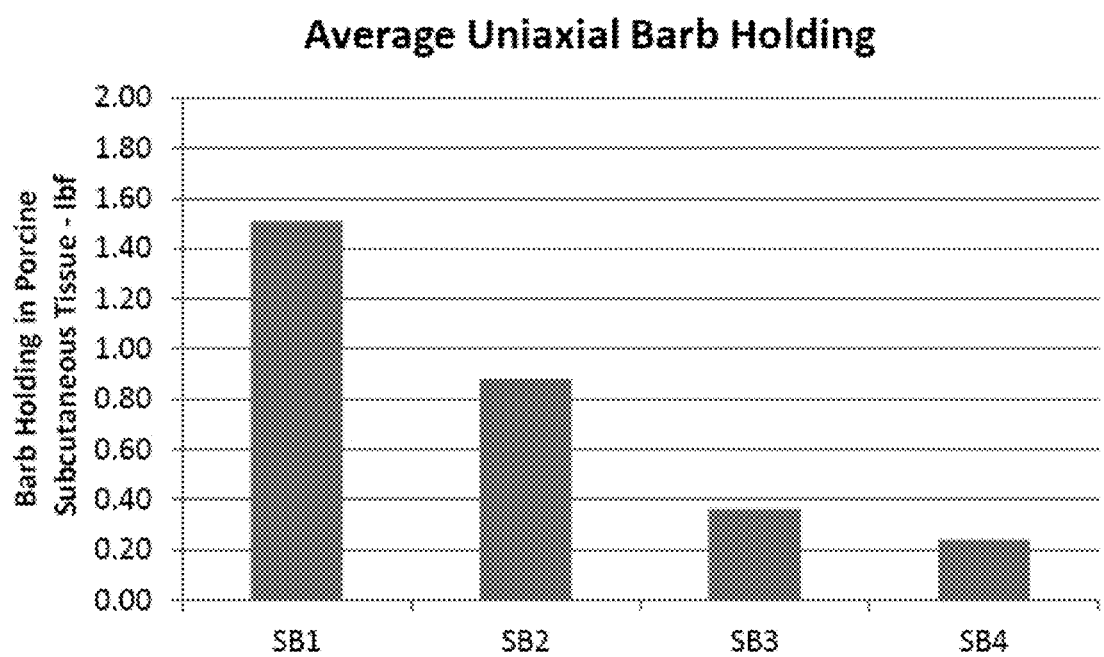
FIG. 7 shows a second graph plotting the barb holding load for each of the four barbed sutures shown in FIG. 5.

Referring to FIGS. 5 and 7, the Instron mechanical tester was then stopped, the tissue and the fixture were flipped over, whereupon the Instron mechanical tester pulled each of the four barbed sutures 130 (SB1), 230 (SB2), 330 (SB3), and 430 (SB4) back through the tissue in the opposite direction DIR2. As noted above, the four barbed sutures 130 (SB1), 230 (SB2), 330 (SB3), and 430 (SB4) were not pulled by the Instron mechanical tester at the same time. Each of the four barbed sutures 130 (SB1), 230 (SB2), 330 (SB3), and 430 (SB4) was tested individually so that only one of the four barbed sutures was pulled by the Instron mechanical tester during any single test. The purpose of the barb holding test was to evaluate the barb holding force of the four barbed sutures, as they engage in tissue. After the drag force test is completed, the slotted fixture is opened (with the device still in the tissue), the tissue is flipped over, re-secured in the fixture, and the non-needle end of the device is secured in the upper grip of the Instron mechanical tester (5500 series or equivalent with 20 lb load cell). The Instron mechanical tester pulled the barbed sutures back through the tissue at 1 inch/min and the maximum barb holding force was recorded. The maximum force for each of the barbed sutures was recorded as the barb holding load (FIG. 7). The barb holding load for the first barbed suture 130 (SB1) was about 1.50 lbf. The barb holding load for the second barbed suture 230 (SB2) was about 0.90 lbf. The barb holding load for the third barbed suture 330 (SB3) was about 0.38 lbf. The barb holding load for the fourth barbed suture 430 (SB4) was about 0.22 lbf.

The data shown in FIGS. 6 and 7 is meaningful for several reasons. First, as shown in FIG. 6, as the barbed sutures are pulled in the first direction DIR1 (FIG. 5), there are negligible differences in tissue drag values for the four barbed suture designs SB1, SB2, SB3, and SB4. A trend emerges in the graph shown in FIG. 7, however, showing that the barb holding strength can be modified to be relatively high or low, by modifying the trailing edge angles of the barbed sutures. For example, the first barbed suture 130 (SB1) having a more acute trailing edge angle is less reversible and may be better suited for high wound tension areas or to plicate tissue, whereas the fourth barbed suture (SB4) having a greater trailing edge angle is more reversible and may have more value in superficial tissue layers where the reversibility feature would enable a surgeon to adjust the tension of the incision line to produce a more favorable cosmetic result.

Example 3

Figure 8:
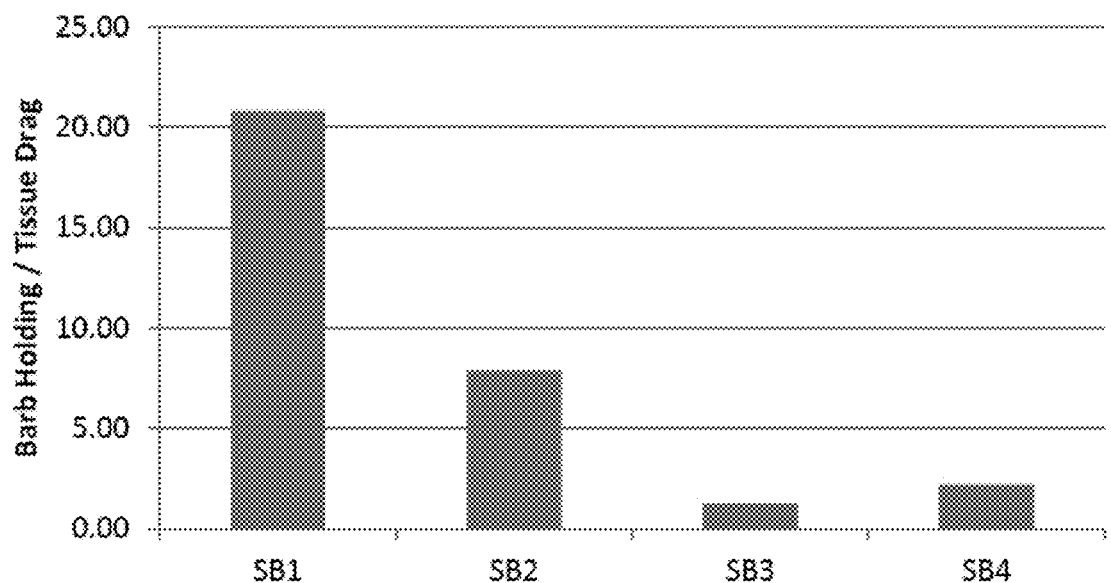
FIG. 8 shows a third graph that indicates the ratio of the barb holding load to the tissue drag for each of the four barbed sutures shown in FIG. 5.

FIG. 8 shows the ratio of the barb holding value to the tissue drag value for each of the four barbed sutures 130 (SB1), 230 (SB2), 330 (SB3), and 430 (SB4). As shown in FIG. 8, the force required to pull the first barbed suture 130 through the tissue in the second direction DIR2 is 20 times greater than the force required to pull the first barbed suture through the tissue in the first direction DIR1. In contrast, for the third barbed suture 330 (SB3) and the fourth barbed suture 430 (SB4), the force required to reverse the suture (i.e., pull in direction DIR2) is about 1-2× the force required to pull the barbed sutures through tissue in the first direction DIR1 (FIG. 5). Although the present invention is not limited by any particular theory of operation, it has been observed that the third and fourth barbed sutures are more reversible because there is a lower ratio between the barb holding load and the tissue drag force.

Example 4

Figure 9:
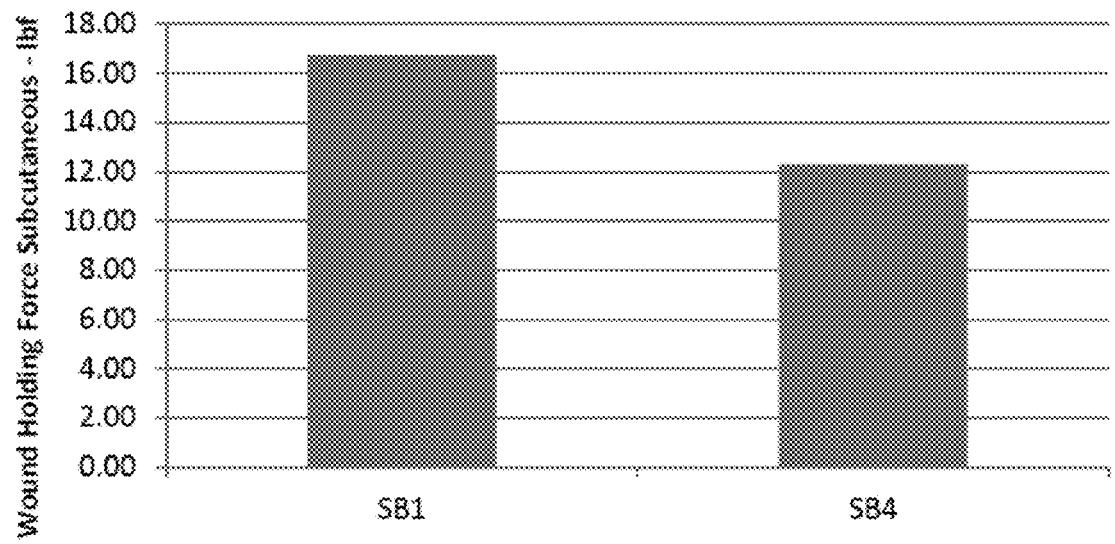
FIG. 9 shows a fourth graph that indicates the wound holding force provided by the first barbed suture shown in FIGS. 1A-1C compared with the fourth barbed suture shown in FIGS. 4A-4D.

Referring to FIG. 9, a third test was conducted whereby two planes of porcine tissue were sutured together at the subcutaneous tissue layer using a continuous stitch pattern. The sutured tissue was then loaded into an Instron mechanical tester and a load was applied perpendicular to the suture line. The maximum force from this test was recorded as the wound holding force as shown in the graph of FIG. 9. This test was completed for the first barbed suture 130 (SB1) and the fourth barbed suture 430 (SB4) to determine the wound holding ability of the two extreme designs of the four barbed suture designs described herein. As shown in the graph in FIG. 9, the wound holding force of the two "extreme" designs (SB1 vs. SB4) is different but comparable. The wound holding force for the first barbed suture 130 (SB1) was about 16.75 lbf. The wound holding force for the fourth barbed suture 430 (SB4) was about 12.25 lbf.

In one embodiment, the wound holding test was designed to measure the holding strength of the barbed sutures in animal or human tissue using varied closure configurations in a bench top model. This method simulates the wound holding force required for a surgical incision to fail. Tissue types include, but are not limited to, deep abdominal tissue, deep superficial fascia, other soft tissue, subcutaneous tissue, or skin. Tissue was prepared by isolating the layer of interest and dissecting the specimen into two halves to represent a surgical incision. Tissue thicknesses were measured and recorded, and testing groups are made up of tissues with similar thicknesses. A template was then applied to the two tissue halves, whereby an incision (typically 6-10 cm in length) was marked for the tissue bites to be spaced 1 cm apart. The suture was then applied in the tissue and spaced according to the template. The suture may be applied using a variety of surgical techniques. The sutured tissue was placed in a custom fixture, which simulated the tension exerted in living tissue. The fixture and sutured tissue were then loaded into an Instron mechanical tester (5500 series or equivalent with 100 lb load cell). The equipment control parameters were as follows: crosshead speed=5 in/min, sampling rate=60 pts/sec, gauge length=2.5 cm (set within the custom fixture). The tests were run until a three inch extension was achieved, or until failure occurred by tissue gapping (5 mm), tissue failure, suture failure, or suture pull-out within a specimen. Maximum load, extension at maximum load, and failure mode were recorded. The tissue holding strength was recorded as the maximum tensile force exerted upon a specimen to cause one of the above-described failure modes.

The data presented in the graphs of FIGS. 6-9 shows that the load recorded when passing the respective barbed sutures 130, 230, 330, 430 through tissue in the first direction DIR1 (FIG. 5) was comparable across the four designs. However, when the barbed sutures were passed through the tissue in the opposite, second direction DIR2, a trend emerged in the barb holding force data, whereby the barb design dictated varying degrees of barb holding resistance or lack of resistance depending on the particular design of the barbed suture. The third and fourth barbed sutures 330 (SB3) and 430 (SB4) provided relatively low barb holding resistance, which supports the concept of adjustability or reversibility. The data also showed that, in the aggregate, the barbs of the first barbed suture 130 (SB1) and the fourth barbed suture 430 (SB4) generated wound holding forces in the range of 16 to 12 lbs, respectively.

The barbed sutures disclosed in the present application may be used for a wide variety of medical applications such as hernia repair, anastomoses, wound closure, closing incisions, organ support (e.g., pexy procedures e.g., with pelvic organ support or tongue support for the treatment of obstructive sleep apnea), trauma repair (where rapid tissue repair is needed), cosmetic procedures, and other surgical procedures requiring a distribution of forces along the surface of tissue to minimize direct suture pressure on tissue. In one embodiment, the barbed sutures may be used for heart valve fixation procedures. In one embodiment, a surgical method includes attaching a needle to a first end of a barbed suture, providing a stop tab at the second end of the barbed suture, passing the first end of the barbed suture through both sides of the beginning end of an incision, utilizing the stop tab at the second end of the barbed suture for providing fixation of the second end of the barbed suture, and then suturing in a continuous pattern (e.g., a helical pattern) to the opposite end of the incision. In one embodiment, in order to adjust the location of the barbed suture, the direction that the barbed suture is pulled through tissue may be reversed for properly approximating tissue without causing tissue trauma and/or plastic deformation and damage to the barbs.

Figure 10:
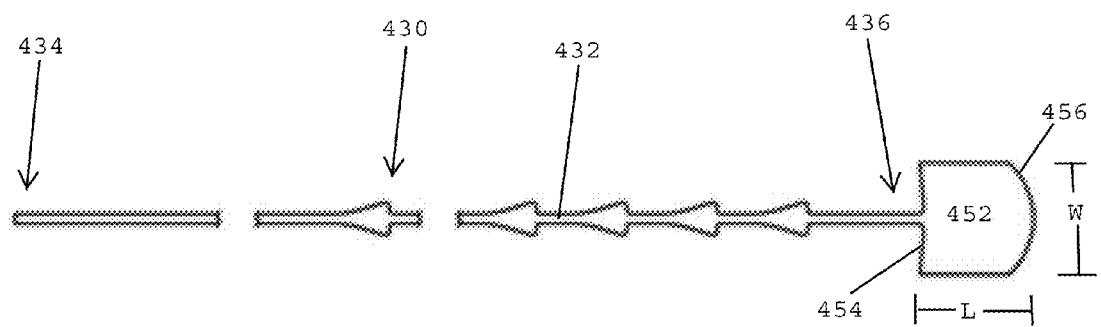
FIG. 10 shows a barbed suture having a first end and an end stop attached to a second end, in accordance with one embodiment of the present invention.
Figure 11:
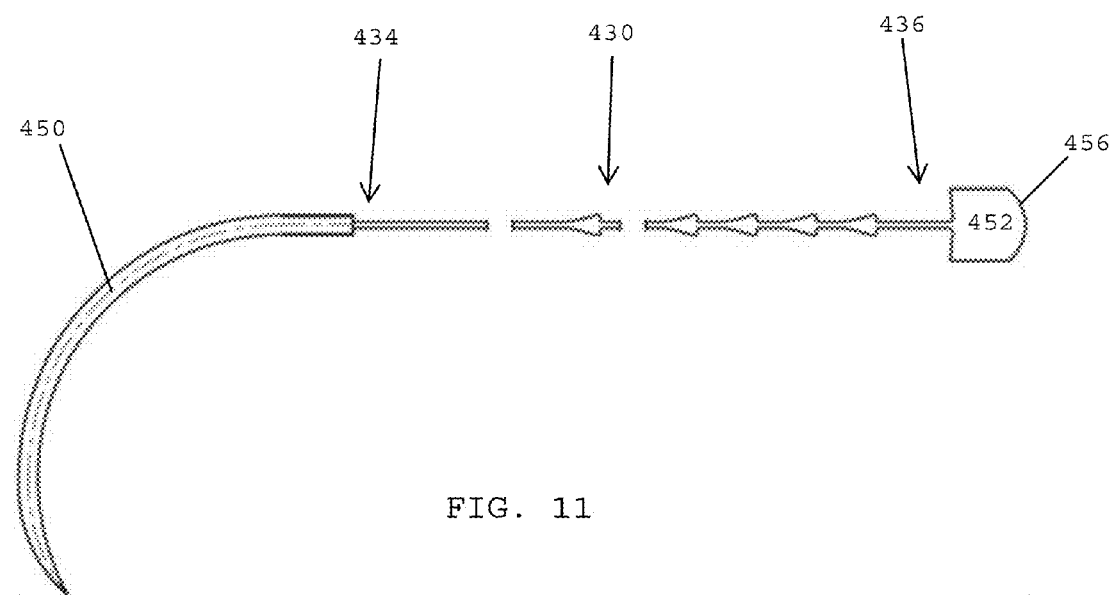
FIG. 11 shows the barbed suture of FIG. 10 with a needle secured to the first end, in accordance with one embodiment of the present invention.

Referring to FIGS. 10 and 11, in one embodiment, a barbed suture 430 has a needle 450 secured to the first end 434 of the filament 432, and a stop tab or fixation tab 452 secured to the second end 436 of the filament 432, as disclosed in commonly assigned U.S. patent application Ser. No. 13/248,542, filed Sep. 29, 2011, and Ser. No. 13/621,625, filed Sep. 17, 2012, the disclosures of which are hereby incorporated by reference herein. The fixation tab 452 desirably has a leading edge 454 having a leading edge thickness (not shown) and a leading edge width W. The fixation tab 452 also desirably has a length L. Although the fourth barbed suture 430 is shown in FIGS. 10 and 11, in other embodiments, any of the other barbed sutures disclosed herein, or incorporated by reference herein, may be attached to the needle 450 and/or the fixation tab 452.

In one embodiment, the fixation tab 452 located at the second end 436 of the filament 432 provides an anchoring element to begin the continuous suture pattern. The size and shape of the fixation tab 452 provide several benefits. The fixation tab 452 is designed to be comprised of a volume of suture material that is less than that of a conventional five-throw knot tower that would typically be used for a monofilament suture knot in the superficial tissue layers. Minimizing the bulk, or mass, of suture material is particularly important in the superficial tissue layers for several reasons. A smaller mass of suture material may reduce the likelihood of palpitation, which is when the patient can feel the implanted bulk of suture material when running one's fingers over the skin's surface. A smaller mass of suture material may also reduce the likelihood of suture "spitting," which may happen if the human body has an adverse reaction to the suture material and essentially extrudes the bulk of suture material up through the skin's surface. The fixation tab 452 has a rounded back end 456 that is preferable for use in the superficial tissue layers because a rounded surface of the rounded back end 456 may be less likely to pierce through the skin's surface and "spit" than the tails of a conventional suture knot. Additionally, the fixation tab 452 provides more surface area than a conventional five-throw knot tower, which may accelerate the degradation process of absorbable suture materials comprising a fixation tab in vivo. Having a fixation tab 452 with less mass than a conventional five-throw knot tower, relatively high surface area, and a rounded back end 456 is believed to result in improved clinical outcomes in cases when used appropriately and depending on the surgical procedure and the individual characteristics of the patient.

Referring to FIGS. 12A-12B, in one embodiment of the present invention, a fifth barbed suture 530 preferably has a configuration and dimensions similar to those described above for the fourth barbed suture 430 (FIGS. 4A-4D). In one embodiment, the fifth barbed suture preferably includes a flexible filament 532 having a first end, a second end, and a longitudinal axis $A_5$ that extends from the first end to the second end 436. The barbed suture 530 includes a plurality of collapsible barbs 538 that project outwardly from the flexible filament 532 (i.e., away from the longitudinal axis $A_5$) and extend toward the second end of the flexible filament 532. The barbed suture preferably includes openings 560 formed in the barbs 538, as disclosed in commonly assigned U.S. Patent Application Publication No. 20090312791, the disclosure of which is hereby incorporated by reference herein. The openings 560 desirably minimize the rigidity and stiffness of the barbs 538, thereby enabling the barbs to collapse inwardly as the barbed suture is pulled in either the first direction DIR1 or the second direction DIR2. In one embodiment, the openings 560 may extend inwardly beyond the outer surface of the filament 532 (i.e., into the core of the filament).

Referring to FIG. 12B, the paired barbs 538A, 538A' extend away from one another on opposite sides of the flexible filament 532. The first barb 538A has first and second lateral side wall 548A, 548B that taper inwardly toward one another between the core of the flexible filament 532 and the blunt tip 544 of the first barb at an angle of about 4°. The inwardly tapering second lateral side wall 548A also defines an angle of about 4°. Each of the lateral side walls of the second barb 538A' also taper inwardly at an angle of about 4°.

Referring to FIGS. 13A and 13B, in one embodiment, a barbed suture 630 has a barb 638 with a double hump. The leading edge 640 of the first barb 638A defines an angle with the longitudinal axis $A_6$ of at least 68° and the trailing edge 646 of the first barb also defines an angle with the longitudinal axis of at least 68°. The second barb 638A' mirrors the shape and dimensions of the first barb 638A. Referring to FIG. 13B, the side walls of the first barb 638A taper inwardly toward the blunt tip 644 at an angle of about 4°. Each of the side walls of the second barb 638A' also taper inwardly at about 4°.

Referring to FIGS. 14A and 14B, in one embodiment, a barbed suture 730 has a pair of barbs 738A, 738A' that define a diamond shape. The leading edge 740 of the first barb 738A defines an angle with the longitudinal axis $A_7$ of at least 68° and the trailing edge 746 of the first barb 738A defines an angle with the longitudinal axis $A_7$ of at least 68°. Referring to FIG. 14B, each of the side walls of the first barb 738A taper inwardly toward the blunt tip 744 at an angle of about 4°. The second barb 738A' mirrors the shape and dimensions of the first barb 738A so that the aligned barbs 738A, 738A' form a diamond shaped element.

Figure 15:
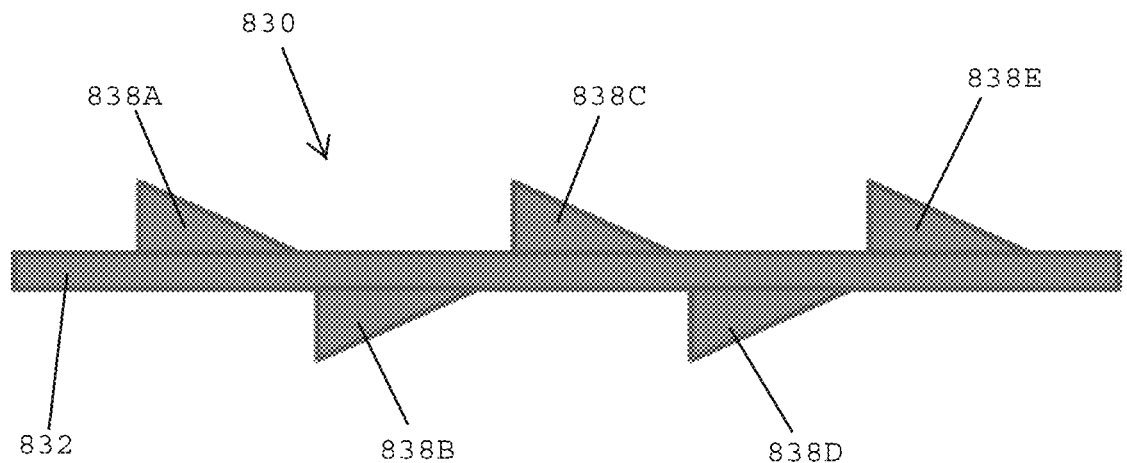
FIG. 15 shows a barbed suture having a core filament and barbed staggered along the length of the filament, in accordance with one embodiment of the present invention.

Referring to FIG. 15, in one embodiment, a barbed suture 830 includes a flexible filament 832 having a plurality of barbs 838 projecting outwardly from the flexible filament. In one embodiment, the barbs 838A-838E are staggered relative to one another along the length of the flexible filament 832.

Figure 16:
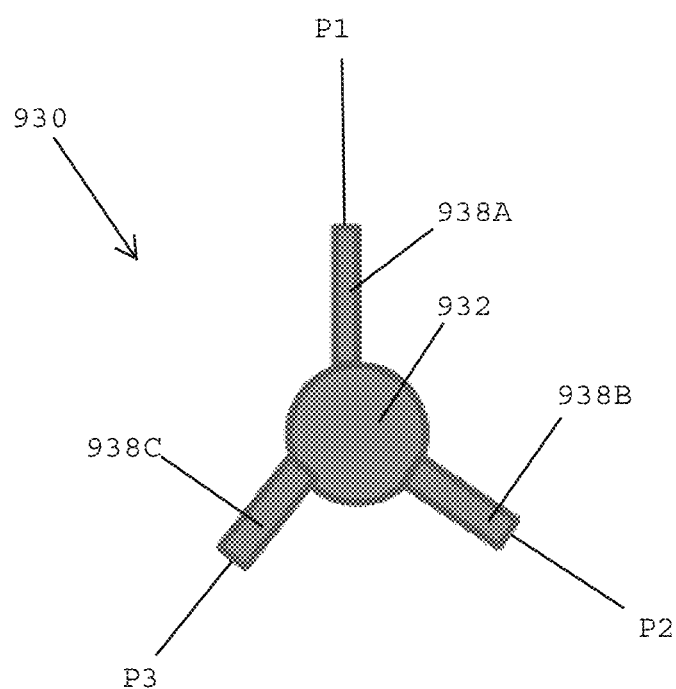
FIG. 16 shows a barbed suture having a core filament and barbs projecting outwardly from opposite sides of the core filament that lie in different planes, in accordance with one embodiment of the present invention.

Referring to FIG. 16, in one embodiment, a barbed suture 930 includes a flexible filament 932 having a plurality of barbs 938 projecting outwardly from the flexible filament. In one embodiment, at least some of the barbs 938A-938C do not lie in a single plane, but project outwardly from the flexible filament 932 in different planes P1, P2, P3. In one embodiment, the barbs may be aligned with one another along the length of the flexible filament, but not lie in a single plane and the barbs preferably project outwardly from the flexible filament in different planes.

In one embodiment, the wound closure device may be made of polymeric, metallic and/or ceramic materials that are absorbable or non-absorbable. In yet another embodiment, the wound closure device may be made of a polymer material selected from absorbable and non-absorbable homopolymers, random copolymers, block copolymers or blends made from polydioxanone, polyglactin, polyglycolic acid, copolymers of glycolide, lactide, and/or caprolactone, polyoxaesters, poliglecaprone, polypropylene, polyethylene, polyvinylidene fluoride (PVDF), hexafluoropropylene, copolymers of vinylidene fluoride and hexafluoropropylene, polyesters, polyethylene terephthalate, polybutylene terephthalate, glycol-modified polyethylene terephthalate, polytetrafluoroethylene, fluoropolymers, thermoplastic elastomers, ionomers, copolymers of ethylene and methacrylic acid, polyamides, polytetramethylene oxide, polystyrene, polybutadiene, and polybutylene, including combinations and/or copolymers of absorbable and non-absorbable materials.

In one embodiment, the barbed suture is made using a non-absorbable polymeric material, and a non-absorbable multi-filament polyester suture, commonly sold under the trademark ETHIBOND EXCEL polyester suture by Ethicon, Inc.

While the foregoing is directed to embodiments of the present invention, other and further embodiments of the invention may be devised without departing from the basic scope thereof, which is only limited by the scope of the claims that follow. For example, the present invention contemplates that any of the features shown in any of the embodiments described herein, or incorporated by reference herein, may be incorporated with any of the features shown in any of the other embodiments described herein, or incorporated by reference herein, and still fall within the scope of the present invention.

What is claimed is:

1. A wound closure device comprising:
   a flexible filament having a first end, a second end, and a longitudinal axis extending between said first and second ends;
   a plurality of barbs projecting outwardly from said flexible filament, each said barb having a base connected with said flexible filament, a blunt tip having a convexly curved surface spaced from said base, a leading edge extending between said base and said blunt tip and facing toward said first end of said flexible filament, and a trailing edge extending between said base and said blunt tip and facing toward said second end of said flexible filament, wherein said trailing edge of said barb and the longitudinal axis of said flexible filament define an angle of at least 68°;
   each said barb further comprising a transition surface defining a concave surface extending from said trailing edge of said barb to an outer surface of said flexible filament, wherein a line perpendicular to the longitudinal axis of said flexible filament contacts the concave surface of said transition surface and contacts the convexly curved surface of said blunt tip tangentially.

2. The wound closure device as claimed in claim 1, wherein said leading edge of said barb defines a concave surface having a radius of about 0.090 inches.

3. The wound closure device as claimed in claim 1, wherein the convexly curved surface of said blunt tip defines a radius of about 0.004 inches.

4. The wound closure device as claimed in claim 1, wherein the concave surface of said transition surface of said barb has a radius of about 0.003 inches.

5. The wound closure device as claimed in claim 1, wherein said flexible filament has a length and said barbs are evenly spaced along the length of said flexible filament.

6. The wound closure device as claimed in claim 5, wherein said blunt tips of said evenly spaced barbs define a tip-to-tip pitch of about 0.070-0.080 inches.

7. The wound closure device as claimed in claim 1, wherein said barbs comprise pairs of barbs evenly spaced along the length of said flexible filament, and wherein said barbs in each said pair are aligned with one another.

8. The wound closure device as claimed in claim 7, wherein said aligned barbs in each said pair project away from one another and are disposed on opposite sides of said flexible filament.

9. The wound closure device as claimed in claim 8, wherein said aligned barbs in each said pair lie in a common plane.

10. The wound closure device as claimed in claim 1, wherein said bases of said barbs are thicker than said blunt tips of said barbs, and wherein each said barb tapers inwardly between said base and said tip at an angle of about 3-5°.

11. The wound closure device as claimed in claim 1, further comprising a needle connected with said first end of said flexible filament.

12. The wound closure device as claimed in claim 1, wherein on each said barb, the concave surface of said transition surface and the convexly curved surface of said blunt tip are aligned with one another along the longitudinal axis of said flexible filament.

13. A wound closure device comprising:
a flexible filament having a first end, a second end, and a longitudinal axis extending between said first and second ends;
a plurality of barbs projecting from said flexible filament, each said barb having a base connected with said flexible filament, a tip spaced from said base, said tip having a blunt surface, a leading edge extending between said base and said tip and facing toward said first end of said flexible filament, and a trailing edge extending between said base and said tip and facing toward said second end of said flexible filament;
each said barb further comprising a transition surface defining a concave surface extending from said trailing edge of said barb to an outer surface of said flexible filament, wherein a line perpendicular to the longitudinal axis of said flexible filament contacts the concave surface of said transition surface and contacts said blunt surface of said tip tangentially, and wherein said trailing edge of said barb and the longitudinal axis of said flexible filament define an angle of at least 68°.

14. The wound closure device as claimed in claim 13, wherein said leading edge of said barb defines a concave surface having a radius of about 0.090 inches, and said blunt surface defines a convex surface having a radius of about 0.004 inches.

15. The wound closure device as claimed in claim 13, wherein the concave surface of said transition surface defines a radius of about 0.003 inches.

16. The wound closure device as claimed in claim 13, wherein the radius of said blunt surface of said tip and the concave surface of said transition surface are aligned with one another along the longitudinal axis of said flexible filament.

17. A wound closure device comprising:
a flexible filament having a first end, a second end, and a longitudinal axis extending between said first and second ends;
a plurality of barbs projecting outwardly from said flexible filament, each said barb having a base connected with said flexible filament, a blunt tip spaced from said base, a leading edge extending between said base and said blunt tip and facing toward said first end of said flexible filament, a trailing edge extending between said base and said tip and facing toward said second end of said flexible filament, and a transition surface extending between said trailing edge and said flexible filament, wherein said leading edge defines a concave surface having a radius of about 0.090 inches, said blunt tip defines a convex surface having a radius of about 0.004 inches and said transition surface defines a concave surface having a radius of about 0.004 inches, and wherein said trailing edge of said barb and the longitudinal axis of said flexible filament define an angle of at least 68°;
the convex surface of said blunt tip and the concave surface of said transition surface being aligned with one another along the longitudinal axis of said flexible filament so that a line passing perpendicularly through the longitudinal axis of said flexible filament contacts the convex surface of said blunt tip tangentially and contacts the concave surface of said transition surface.

18. The wound closure device as claimed in claim 17, wherein said barbs are evenly spaced along the length of said flexible filament and define a longitudinal tip-to-tip pitch of about 0.070-0.080 inches, and wherein said plurality of barbs includes pairs of barbs that are aligned with one another and evenly spaced along the length of said flexible filament, said barbs in each said pair projecting away from one another and being disposed on opposite sides of said flexible filament.

* * * * *